(12) United States Patent
Lett

(10) Patent No.: US 10,105,312 B2
(45) Date of Patent: Oct. 23, 2018

(54) HAIR GROWTH OIL COMPOSITION

(71) Applicant: Keisha Lett, Waxahachie, TX (US)

(72) Inventor: Keisha Lett, Waxahachie, TX (US)

( * ) Notice: Subject to any disclaimer, the term of this patent is extended or adjusted under 35 U.S.C. 154(b) by 28 days.

(21) Appl. No.: 15/372,479

(22) Filed: Dec. 8, 2016

(65) Prior Publication Data

US 2017/0172906 A1 Jun. 22, 2017

Related U.S. Application Data

(60) Provisional application No. 62/268,562, filed on Dec. 17, 2015.

(51) Int. Cl.
*A61K 36/00* (2006.01)
*A61K 8/92* (2006.01)
*A61Q 7/00* (2006.01)
*A61K 8/97* (2017.01)
*A61K 8/67* (2006.01)

(52) U.S. Cl.
CPC .............. *A61K 8/925* (2013.01); *A61K 8/678* (2013.01); *A61K 8/922* (2013.01); *A61K 8/97* (2013.01); *A61Q 7/00* (2013.01)

(58) Field of Classification Search
CPC ...................................................... A61K 36/00
See application file for complete search history.

(56) References Cited

U.S. PATENT DOCUMENTS 9,066,952 B1 * 6/2015 Brown .................... A61K 36/53
2011/0305681 A1 * 12/2011 Anderson ................ A61K 8/46
424/94.1

* cited by examiner

*Primary Examiner* — Qiuwen Mi
(74) *Attorney, Agent, or Firm* — Frank Huy Pham; Pham IP Group

(57) ABSTRACT

A hair growth oil composition to be applied topically to the human scalp in order to encourage hair growth. The present invention accomplishes these goals through a mixture of ingredients precisely proportioned to achieve a unique chemical composition that brings about maximum results. The ingredients in the composition include coconut oil, emu oil, bhringaraj (*eclipta alba*), amalaki (*emblica officinalis*), vitamin E, and pharmaceutically acceptable excipients are described. A method of use is also disclosed.

4 Claims, No Drawings

HAIR GROWTH OIL COMPOSITION

CROSS-REFERENCE TO RELATED APPLICATION

The present application is based on, and claims the benefit of priority of U.S. application Ser. No. 62/268,562 filed on Dec. 17, 2015, the disclosure of which is hereby incorporated by reference herein in its entirety.

BACKGROUND

1. Field of the Invention

The present preferred embodiment relates to hair growth oil composition to be applied topically to the human scalp to produce hair growth naturally. The ingredients include hair growth herbs and oils with capability to penetrate through the human scalp and to stimulate the hair follicles that results in making the cells in the hair bulb divide and hair growth.

2. Description of the Prior Art

Hair loss afflicts huge numbers of men and women, and inspires in its sufferers an ardent desire to solve the problem. This desire can be seen by the large number of inventions that have been created to stop hair loss. There have been a myriad of patented products to promote scalp health and generate the growth of hair. As in any field of application, there is always room for improvement.

This application relates to hair sprout oil composition for hair growth purposes, specifically utilizing emu oil, and method of making and using the hair sprout oil compositions.

Numerous compositions that induce hair growth and scalp health have received patents throughout the years, and it would be impossible to list references to all or even most of them. However, most patented compositions are comprised of a distinct mix of conventional ingredients combined in a uniquely proportionate manner. The present invention is based upon this legacy with an ingenious recipe for the most effective promotion of hair growth and overall scalp health.

Accordingly, there is a need for better forms of hair growth compositions having high levels of purities for pharmaceutical use to minimize the potential side effects in patients using hair growth composition products. In particular, there is an existing need for stable hair sprout composition.

SUMMARY OF THE INVENTION

The present invention relates to a safe and efficient hair growth chemical composition composed of a variety of substances mixed according to a strict proportionate formula. When these substances are combined in the proportions specified in the present invention, the resultant unique composition confers upon the user numerous benefits relating to hair growth and the health of the user's scalp.

In another embodiment, the hair growth oil composition comprises ultrapure emu oil, wherein the ultrapure emu oil comprises no more than 3.0% total impurities, preferably no more than about 2.0% total impurities, pharmaceutically acceptable excipients, bhringaraj (*eclipta alba*), amalaki (*emblica officinalis*), and Vitamin E.

The benefits of the present preferred embodiment, besides the stimulation of hair growth, the hair growth oil composition does not clog the scalp but penetrate it and reaches the hair follicle. As a result, there are no potential side effects with the extended use of hair sprout oil composition.

Method of making the hair growth oil composition is also disclosed herein.

In an embodiment, the method of making hair sprout oil composition comprises bhringaraj and amalaki with pharmaceutically acceptable excipients, and mixing the bhringaraj and amalaki with coconut oil to obtain a mixture.

Heating time is generally about 4 to 10 hours. In one embodiment, the mixture and coconut oil may be mixed with water for a period of about 5 to about 45 minutes, or more specifically, about 5 to about 35 minutes. For a small scale, the mixing time is about 1 to about 20 minutes, or more specifically, 3 to 10 minutes. This process is generally performed by heating and evaporation on a stirrer plate between about 100° F. to about 300° F., or more specifically, at 250° F.

Any equipment may be used to contact the mixture and the excipients as long as uniform distribution of the mixture liquid is achieved. For example, small-scale production can be achieved by mixing and wetting the bhringaraj and amalaki and any excipients in jars or stainless steel bowls, while for larger quantities, planetary mixers, rotary granulators, high shear granulators, and fluid-bed granulation equipment may be used.

Mixing can be carried out for a sufficient time to produce homogeneous mixtures or blends. Mixing may be accomplished by blending, stirring, shaking, tumbling, rolling, or by any other method to achieve a homogeneous blend. In some embodiments, the components to be mixed are combined under low shear conditions in a suitable apparatus capable of functioning under low shear conditions.

In another embodiment, the method of making hair growth oil composition, mixing the separated oil from the above mixture with ultrapure emu oil, wherein the ultrapure emu oil comprises no more than about 3.0% of total impurities, preferably no more than about 2.0% total impurities, with pharmaceutically acceptable excipients, to obtain the composition.

The hair growth oil composition of this invention may be made into a wide variety of product types that include but are not limited to solid and liquid compositions such as lotions, creams, gels, sticks, sprays, ointments, cleansing liquid washes and solid bars, shampoos, pastes, powders, foams, mousses, and wipes. These product types may contain several types of cosmetically acceptable topical carriers including, but not limited to compositions, emulsions, gels, solids and liposomes. Other carriers can be formulated by those of ordinary skill in the art.

Disclosed herein also a method of using hair growth oil composition.

The hair growth oil composition of the preferred embodiment may be utilized to induce hair growth by topical application of said composition to the area of the body on which hair growth is desired. Preferably, the hair growth oil composition of this invention are applied topically to the desired area of the body at least once per day for at least three weeks but preferably on a daily for at least fourteen weeks and more preferably, indefinitely. For better result, said hair growth oil composition should be applied at least once per day for at least six weeks. After six weeks, the user should observe increased hair growth and should be able to observe increased hair shaft diameter and/or enhanced visual attributes of the hair, such as hair volume, hair shine and hair thickness.

DETAILED DESCRIPTION OF THE DISCLOSURE

The present invention is a hair growth oil composition composed of a variety of substances mixed according to a strict proportionate formula. When these substances are combined in the proportions specified in the present invention, the resultant unique chemical composition confers upon the user numerous benefits relating to hair growth and the health of the user's scalp.

Table A shown below shows the percentage of each ingredient found within any quantity of the present invention.

TABLE A

| INGREDIENT | % OF TOTAL |
| --- | --- |
| Coconut oil | 23 |
| Emu oil | 30 |
| Bhringaraj (*eclipta alba*) | 20 |
| Amalaki (*emblica officinalis*) | 21 |
| Vitamin E | 6 |

Below are brief explanations of the ingredients found in the present invention. Coconut oil is exceptionally rich and contains fatty acids that stimulate the skin's natural renewal processes and replenish lost oils to the scalp and hair, leaving it healthy and shiny. Because it is rich in Vitamins A and E, coconut oil soothes dryness, repairs breakage and mends split ends.

Extra virgin coconut oil is a light and penetrating oil that is cold-processed from fresh coconut milk. Extra virgin coconut oil is non-greasy, high in Vitamin E, and highly valued for its conditioning properties. It hydrates the scalp, produces shiny hair, and stimulates hair growth.

Emu oil is absorbed quickly and completely into the scalp without clogging pores, without leaving a greasy residue, and without causing build-up of oil or dandruff. Emu oil also helps heal a variety of scalp conditions, including dry scalp, psoriasis, eczema and dermatitis. It is rich in moisture and can shield against harmful ultraviolet radiation, protecting the hair from sun damage.

Emu oil is also known as a soothing and lubricating oil that is rich in fatty acids and acts as a humectant by attracting moisture to the hair and skin. Emu oil is superb for its conditioning and moisturizing properties, helping the ends of a user's hair become shiny and hiding the appearance of frizzy, damaged, and split ends. It reduces and prevents hair damage, leading to thicker and fuller hair for the user, and stimulates hair growth.

Bhringaraj and amalaki combine to bring about a unique building of body for the hair. With this combination, the Amalaki ingredient acts to condition and nourish the hair and hair follicles, while the Bhringaraj ingredient helps strengthen and add body to the hair. Both bhringaraj and Amalaki also promote hair growth.

Vitamin E (tocopherol) is an anti-oxidizing agent that helps to stabilize oils and prevent rancidity. Vitamin E (tocopherol) also has anti-oxidizing properties for the skin, promotes healing, and improves circulation within the scalp.

The combination of but not limited to coconut oil, emu oil, bhringaraj, and amalaki is agent for stimulating hair growth. The present invention, however, does more than stimulate hair growth. It also moisturizes and conditions the user's hair, controls dandruff and itchy scalp, treats psoriasis, repairs damaged hair, controls frizzy hair, gives hair a smooth look and feel, minimizes hair shedding, strengthens and thickens the hair, makes hair softer and more manageable, builds hair body, and restores luster and shine to the hair. The composition is non-greasy and is envisioned to be used on all types of hair. The result of the preferred embodiment of the present invention is an oil-like composition.

The present invention is meant to be applied daily or every other day on problem areas of the scalp body. It should be left on hair or problem areas for at least 20 minutes, or even overnight. For maximum effect, the user should not apply heat to the problem areas in order that the oils within the present invention will be encouraged to go into the hair shaft.

The present invention is envisioned to be applied sparingly to the scalp and throughout the ends of the hair as needed. In this embodiment, the present invention is employed as a leave-in conditioner, which is preferably employed once a week. The present invention is preferably applied to problematic areas daily, or every other day.

The present invention may also be applied to normal and/or dry hair as a deep conditioner. First, prior to shampooing the hair, apply the present invention to the scalp and throughout the hair to the ends. Next, cover the scalp with a plastic cap for approximately 20 to 30 minutes, or even overnight. It is via this method that the hair is deep conditioned. Next, simply shampoo the hair; then detangle the hair with a light conditioner for preferably one to two minutes. Finally, rinse and style the hair.

In the event that the present invention is to be applied to dry or damaged hair, the following method of use is preferred: first, prior to shampooing the hair, apply the present invention to the scalp and throughout the hair to the ends, second, cover the scalp with a plastic cap. The hair may be left in this position overnight if an intense conditioning is needed. Next, shampoo the hair, and then detangle the hair with a light conditioner for preferably one to two minutes. Finally, rinse and style the hair as needed.

It is envisioned that the present invention is not limited as to the duration of use on hair. It is encouraged, however, to be applied to hair consistently in order to achieve the best results, and maintain healthy strong hair.

Example 1

A research study of human participants with hair growth oil composition was carried out to show the effectiveness of the hair growth oil composition of the present invention. A fixed combination of the oil composition containing ingredients by weight/total composition weight is administered at least once daily for 2 weeks to users. At the end of the 2-week period most users will demonstrate a significant increase in the activity of their hair growth.

Table C shows the results of applying the oil composition to each participant once daily. Clinical appraisal was carried out at biweekly intervals.

TABLE C

Clinical Evaluation of Hair Growth Oil (% hair growth)

| | Evaluation Time (Weeks) | | | |
| --- | --- | --- | --- | --- |
| Participant | 2 | 4 | 6 | 8 |
| A | 25% | 50% | 48% | 46% |
| B | 65% | 62% | 62% | 62% |
| C | 65% | 98% | 71% | 62% |
| D | — | 62% | 62% | 62% |
| E | 22% | 87% | 52% | — |

TABLE D

| PARTICIPANT | AGE | GENDER |
|---|---|---|
| A | 25 | F |
| B | 38 | F |
| C | 40 | F |
| D | 41 | F |
| E | 34 | M |

The results of the foregoing tests show that the oil composition consistently used in the systemic treatment of hair loss is essentially effective in the first four weeks. Overall, the results of the foregoing tests show a good improvement for all participants.

Example 2

The study of Example 1 is repeated to show the efficacy and safety of the oil composition of the present invention (Table F). Safety and tolerability were assessed through evaluations of local tolerability and adverse events. At each visit, the investigator rated the percentage of hair growth on a scale.

The efficacy variables were percent hair growth from previous measurements and participant's measurements of hair growth on a scale from 0 (marked improvement) to 5 (worse) as shown in Table E.

The research study conducted efficacy evaluations consisting of hair growth. Table F is a flow chart of assessed measurements during this study.

TABLE E

| 1 | Marked Improvement |
|---|---|
| 2 | Moderated Improvement |
| 3 | Minimal Improvement |
| 4 | No Change |
| 5 | Worse |

Local tolerability measures of the irritation of skin were considered adverse effects only if the severity of the unexpected signs and symptoms was such that an interruption of the participant's participation in the study, at his/her request or at the investigator's discretion, had occurred. Altered frequency of use (such as every other day use) to manage irritation were not considered to be an interruption of the participant's participation in the study.

The results of the study are shown in Table F below.

TABLE F

| Efficacy and Safety Measurements | | | | |
|---|---|---|---|---|
| | Evaluation Time (Weeks) | | | |
| Participant | 2 | 4 | 6 | 8 |
| Efficacy | | | | |
| A | 3 | 3 | 3 | 2 |
| B | 3 | 3 | 2 | 1 |
| C | 3 | 2 | 1 | 1 |
| D | 3 | 2 | 1 | 1 |
| E | 3 | 1 | 2 | — |
| Safety | | | | |
| A | 3 | 3 | 3 | 2 |
| B | 3 | 3 | 2 | 2 |
| C | 3 | 2 | 1 | 1 |
| D | 2 | 1 | 1 | 1 |
| E | 2 | 1 | 3 | — |

As this was an open-label study, only descriptive data presentations were made. No formal statistical hypotheses were tested. Descriptive statistics were used to summarize all data.

Treatment with hair growth oil composition for up to 4 weeks showed continuing significant improvement starting week 4. The greatest increase of hair growth was seen after 6 weeks of treatment.

In conclusion, the hair growth oil composition of the present invention was well-tolerated and effective in the treatment of hair loss. Signs and symptoms of skin irritation (erythema, dryness, scaling, and stinging/burning) were mostly none or mild and were transient.

Safety findings were consistent with the known profile of ingredients of the oil composition. No unexpected, either systemic or dermatological, evidence of cumulative toxicity was observed over time. Consequently, extending hair treatment beyond 6 weeks does not suggest substantial additional risk for the participants.

The efficacy of oil composition showed continuing increase greater than 65% in all participants treated for 6 weeks.

Invention and its practical application to persons who are skilled in the art. As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

Having illustrated and described the principles of the present invention in a preferred embodiment, it will be apparent to those skilled in the art that the embodiment can be modified in arrangement and detail without departing from such principles. Any and all such embodiments are intended to be included within the scope of the following claims.

What is claimed is:

1. A hair growth composition for hair comprising:
   (a) about 23% by weight of coconut oil;
   (b) about 30% by weight of emu oil;
   (c) about 20% by weight of *eclipta alba;*
   (d) about 21% by weight of *emblica officinalis;*
   (e) about 6% by weight of vitamin E; and
   (f) pharmaceutically acceptable excipients.

2. The hair growth composition for hair of claim 1 wherein said coconut oil, emu oil, *eclipta alba, emblica officinalis,* vitamin E, and pharmaceutically acceptable excipients are evenly distributed.

3. The hair growth composition for hair of claim 2 wherein emu comprises about 3% total impurities.

4. The composition of claim 1 is administered topically.

* * * * *